(12) United States Patent
Dupuis

(10) Patent No.: US 6,803,047 B1
(45) Date of Patent: Oct. 12, 2004

(54) VAPORIZABLE GELLED COMPOSITION

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/380,888

(22) PCT Filed: Mar. 4, 1998

(86) PCT No.: PCT/FR98/00423

§ 371 (c)(1),
(2), (4) Date: Oct. 27, 1999

(87) PCT Pub. No.: WO98/41184

PCT Pub. Date: Sep. 24, 1998

(30) Foreign Application Priority Data

Mar. 14, 1997 (FR) ............................................. 97 03118

(51) Int. Cl.$^7$ ............................. A61K 6/00; A61K 7/00; A61K 9/00; A61K 9/04; A01N 25/02
(52) U.S. Cl. ...................... 424/401; 424/43; 424/70.1; 424/70.11; 424/78.03; 514/506; 514/532; 514/944
(58) Field of Search ........................... 424/401, 43, 47, 424/70.1, 76.11, 78.03; 514/532, 944, 506

(56) References Cited

U.S. PATENT DOCUMENTS

| | | | |
|---|---|---|---|
| 2,047,398 A | | 7/1936 | Voss et al. |
| 2,723,248 A | | 11/1955 | Wright |
| 3,836,537 A | | 9/1974 | Boerwinkle et al. |
| 4,128,631 A | | 12/1978 | Lundmark et al. |
| 4,300,580 A | * | 11/1981 | O'Neill et al. ............... 132/203 |
| 5,066,414 A | * | 11/1991 | Chang ......................... 510/524 |
| 5,705,474 A | * | 1/1998 | Severns et al. ............. 510/500 |
| 5,804,025 A | * | 9/1998 | Disselbeck et al. ...... 156/274.4 |
| 5,830,438 A | * | 11/1998 | Dupuis ......................... 424/45 |
| 6,020,420 A | * | 2/2000 | George ......................... 524/609 |
| 6,031,043 A | * | 2/2000 | Dupuis et al. ............... 524/603 |

FOREIGN PATENT DOCUMENTS

| | | |
|---|---|---|
| DE | 2 330 956 | 1/1974 |
| EP | 0 337 354 | 10/1989 |
| EP | 0 551 748 | 7/1993 |
| EP | 0 551 749 | 7/1993 |
| FR | 1 222 944 | 6/1960 |
| FR | 1 400 366 | 12/1965 |
| FR | 1 564 110 | 4/1969 |
| FR | 1 580 545 | 9/1969 |
| FR | 2 198 719 | 4/1974 |
| FR | 2 265 781 | 10/1975 |
| FR | 2 265 782 | 10/1975 |
| FR | 2 270 846 | 12/1975 |
| FR | 2 350 384 | 12/1977 |
| FR | 2 357 241 | 2/1978 |
| FR | 2 439 798 | 5/1980 |
| FR | 2 470 596 | 6/1981 |
| FR | 2 519 863 | 7/1983 |
| FR | 2 598 611 | 11/1987 |
| GB | 0 839 805 | 6/1960 |
| WO | WO 94/16808 | 8/1994 |
| WO | WO 95/00105 | 1/1995 |
| WO | WO 95/33436 | 12/1995 |
| WO | WO 95/33437 | 12/1995 |

OTHER PUBLICATIONS

English language Derwent Abstract of DE 2 330 956.
English language Derwent Abstract of FR 1 564 110.
English language Derwent Abstract of FR 1 580 545.
English language Derwent Abstract of FR 2 265 781.
English language Derwent Abstract of FR 2 265 782.
English language Derwent Abstract of FR 2 270 846.
English language Derwent Abstract of FR 2 350 384.
English language Derwent Abstract of FR 2 357 241.
English language Derwent Abstract of FR 2 439 798.
English language Derwent Abstract of FR 2 470 596.
English language Derwent Abstract of FR 2 519 863.
English language Derwent Abstract of FR 2 598 611.

* cited by examiner

*Primary Examiner*—Sreeni Padmanabhan
*Assistant Examiner*—Lauren Q. Wells
(74) *Attorney, Agent, or Firm*—Finnegan, Henderson, Farabow, Garrett & Dunner, L.L.P.

(57) ABSTRACT

A topical composition containing an aqueous gel which contains a hydrophilic gelling material, wherein the gel has at least one of the following properties: an initial viscosity $V_0$ ranging from 3000 to 50,000 Pa.s, wherein the initial viscosity is stable up to a shear strain $C_1$, a viscosity $V_2$ after shear at a strain $C_2$, wherein a ratio of $V_0/V_2$ is greater than or equal to 1000, and a difference of $C_2$–$C_1$ is less than or equal to 100 Pa.

33 Claims, No Drawings

VAPORIZABLE GELLED COMPOSITION

The present invention relates to a novel vaporizable topical composition consisting of an aqueous gel comprising a specific hydrophilic gelling material. The invention also relates to a device consisting of a container containing the above cosmetic composition and a means for distributing the said composition, more particularly a pump-dispenser bottle or an aerosol device.

To prepare aerosols which are vaporizable in all positions, expensive specific devices are currently used, involving complex mechanical solutions such as specific valves or systems of pockets which are relatively impractical to implement.

The Applicant has now found that by using a gel which has a specific rheological profile, it is possible to obtain a gelled composition which can be vaporized by standard pump-dispenser bottle and aerosol equipment in all positions.

Common gelling materials, such as guar gums, the Carbopols® sold by the company Goodrich, Sepigel® 305 sold by the company SEPPIC, or thickeners of latex type, such as the Acrysols® sold by the company Rohm & Haas, or Viscoatex® 538 sold by the company Coatex, give gels which do not have the rheological profile of the gels according to the invention and thus cannot be vaporized.

It is also known practice to use alumina to obtain vaporizable, so-called "rheofluidizing" gels (WO 94/16808). However, as with all gels of this type described in the prior art, it is necessary to shake the bottle containing the composition vigorously in order to fluidize it and make its vaporization possible.

The gels which have the specific rheological profile according to the invention are a solution to the problems outlined above.

The present invention thus relates to a composition consisting of an aqueous gel comprising a hydrophilic gelling material, the said gel having the following rheological profile:

- an initial viscosity $V_0$ of between 3000 and 50,000 Pa.s, the said initial viscosity $V_0$ being stable up to a shear strain $C_1$,
- a viscosity $V_2$ after shear at a strain $C_2$ for which the ratio $V_0/V_2$ is greater than or equal to 1000,
- the difference $C_2-C_1$ being less than or equal to 100 Pa.

The gel has an initial viscosity which is stable, i.e. constant at low shear strains, such that the composition can be handled without resulting in a substantial change in its viscosity. This stability of the initial viscosity is expressed by a value of the viscosity of the gel, $V_1$, measured at the shear strain $C_1$ close to $V_0$. It is understood that this proximity should be assessed with regard to the fall in viscosity after shear. Advantageously, the ratio $V_0/V_1$ is less than or equal to 2.

The shear strain $C_1$ is characteristic of the force required to obtain fluidization of the gel, in particular allowing its vaporization. This strain $C_1$ is preferably greater than or equal to 50 Pa. A person skilled in the art will know how to determine the value which this strain should not exceed, as a function of the use which he or she intends to make of the composition according to the invention.

For use in a device allowing its vaporization, the maximum shear strain values $C_1$ can be illustrated below as a function of the vaporization device.

When the means for distributing the composition according to the invention is a pump-dispenser bottle, the maximum shear strain value $C_1$ is preferably less than or equal to 150 Pa.

When the means for distributing the composition according to the invention is an aerosol device, the maximum shear strain value $C_1$ is preferably less than or equal to 200 Pa.

It is understood according to the text hereinabove and hereinbelow that the various viscosity and strain values are measured once the gel has been formed. Before carrying out the viscosity and rheological profile measurements on the gel, it should be ensured that the gel has formed correctly and is stable. It is thus advisable to wait at least 24 hours after preparation of the gel.

Preferably, the falls in viscosity induced by shear on the gel are not immediately reversible, i.e. the material does not break under high strain and remains homogeneous when it has reached its lowest viscosity.

The hydrophilic gelling material according to the invention consists of any gelling material which can form a gel or a composition having the appearance of a gel and having the rheological profile according to the invention.

According to one preferred embodiment of the invention, the hydrophilic gelling material is a hydrophilic gelling polymer. Hydrophilic gelling polymers which are useful according to the invention are, in particular, sulphone polyesters with a weight-average molecular mass of less than 20,000, preferably less than 15,000.

Such polymers can be, more particularly, water-soluble or water-dispersible terephthalic copolyester oligomers essentially comprising dicarboxylate repeating units of formula (I):

$$Co{-}A{-}Co{-}O{-}(CH_2CH_2O)_n \qquad (I)$$

in which

A represents a 1,4-phenylene, sulpho-1,3-phenylene and optionally 1,3-phenylene group,

- n ranges from 1 to 4,
- at least 35 mol % of the said units of formula (I) being units of formula (I) for which A represents a 1,4-phenylene group and n is equal to 1,
- at least 7 mol % of the said units of formula (I) being units of formula (I) for which A represents a sulpho-1,3-phenylene group,
- the weight-average molecular mass of the said copolyester oligomers being less than 20,000, preferably less than 15,000.

Preferably, at least 40 mol %, more preferably between 40 and 90 mol %, of the units of formula (I) are units of formula (I) for which A represents a 1,4-phenylene group and n is equal to 1.

Preferably, at least 10 mol %, more preferably between 10 mol % and 25 mol %, of the units of formula (I) are units of formula (I) for which A represents a sulpho-1,3-phenylene group.

The ends of the chains of the said copolyester oligomers can be similar or different and can be represented essentially by the groups of formula (I'):

$$Co{-}A{-}Co{-}O(CH_2CH_2O)_n{-}OH \qquad (I')$$

in which A and n are defined above.

The said oligomers can also have at the chain ends, and in smaller amounts, groups of formulae $$-A{-}CO{-}OH$$

$$-A{-}CO{-}OR$$

in which formulae A is defined above and R represents a $C_1$–$C_4$ alkyl group.

When A represents a sulpho-1,3-phenylene group, it is more particularly an alkali metal sulphonate, in particular sodium or potassium sulphonate, or an ammonium or lower mono-, di-, tri- or tetraalkylammonium sulphonate. According to the invention, the term lower alkylammonium is preferably understood to refer to an ammonium in which the alkyl radical(s) is(are) lower alkyls, preferably $C_1$–$C_6$ alkyls. Preferably, it is a sodium sulphonate.

The copolyester oligomer can optionally comprise up to 20 mol %, preferably up to 5 mol %, of units of formula (I) for which A represents a 1,3-phenylene group.

According to a preferred embodiment of the invention, the above copolyester oligomer has a weight-average molecular mass of between 5000 and 14,000, more preferably of between 8000 and 10,000.

The weight-average molecular masses are measured by gel permeation chromatography in dimethylacetamide containing $10^{-2}$ N of LiBr, at 100° C. The results are expressed in polystyrene equivalents.

The said copolyester oligomers can be obtained by the usual molten-route, solvent-route or interface-route processes for preparing polyesters, these processes involving esterification reactions of diacids and of diols and polycondensation transesterification reactions of diesters and of diols and polycondensation autocondensation reactions of hydroxy acids Schotten-Baumann reactions using diols and acid chlorides and polycondensation polymerization reactions of lactones while controlling the minimum content of units of formula (I) for which A represents a 1,4-phenylene group and n is equal to 1, which are similar on the basis of the initial stoichiometric ratios of the various monomers and on the basis of the control of the side reactions.

A particularly advantageous mode of preparation is that by mol %en-route transesterification/polycondensation and/or esterification/polycondensation using a transesterification and/or esterification catalyst.

The control of the structure is obtained by controlling the minimum content of units of formula (I) for which A represents a 1,4-phenylene group and n is equal to 1, which are similar on the basis of the initial stoichiometric ratios of the various diacid and/or diester and diol monomers and on the basis of the use of an etherification-limiting agent, it being possible for this limiting agent to be a basic compound such as aliphatic or aromatic amines, or an alkali-metal or alkaline-earth metal hydroxide or acetate.

The control of the molecular mass is obtained in a manner which is known to those skilled in the art, by achieving a suitable compromise between pressure, temperature and time.

The novel terephthalic copolyester oligomers which form the subject of the invention can be prepared by esterification and/or transesterification/poly-condensation of a monomer composition based:

on terephthalic (Tp) acid, anhydride or diester on sulphoisophthalic (SIp) acid, anhydride or diester optionally on isophthalic (Ip) acid, anhydride or diester, and on ethylene glycol (EG)

in relative amounts corresponding to an (SIp)/[(Tp)+(SIp)+(Ip)] molar ratio of at least $7/100$, preferably of at least $10/100$, most particularly of from $10/100$ to $25/100$ an (Ip)/[(Tp)+(SIp)+(Ip)] molar ratio of not more than $20/100$, preferably of not more than $5/100$ an (EG)/[(Tp)+(SIp)+(Ip)] molar ratio of from 2/1 to 3/1 in the presence of an esterification and/or transesterification catalyst and an etherification-limiting agent.

The terephthalic (Tp) monomer is preferably used in the form of a lower diester (di($C_1$–$C_4$)alkyl diester), preferably the dimethyl diester.

The sulphoisophthalic (SIp) monomer is preferably used in the form of an alkali metal sulphonate (in particular sodium sulphonate) of a lower ($C_1$–$C_4$ alkyl), preferably methyl, diester. Sodium dimethyl 5-oxysulphonylisophthalate may be mentioned most particularly.

The optional isophthalic (Ip) monomer is preferably used in the form of isophthalic acid.

When all of the "diacid" monomers are used in the form of diesters, the transesterification (exchange) operation between these "diacid" monomers and ethylene glycol is carried out at a temperature above or equal to 130° C., preferably of about 140 to 220° C. and most particularly of about 180 to 220° C.; at this temperature, the methanol (in the preferred case of the dimethyl diesters) formed is preferably removed from the reaction medium by distillation.

This exchange operation is carried out in the presence of a metallic transesterification catalyst and an etherification-limiting agent. The said catalyst is preferably a metal carboxylate, such as manganese acetate, zinc acetate, cobalt acetate or calcium acetate, or an organic or inorganic titanate such as butyl titanate, nitrilo-2,2',2"-triethyl titanate (or titanium aminotriethanolate which also acts as etherification-limiting agent) or calcium titanate. The preferred catalysts are the organic titanates; they are used in amounts of at least about $^-0.001\%$ by weight, expressed as titanium, preferably from about 0.002% to 0.02% by weight of titanium relative to the weight of reactants present.

The etherification-limiting agent can be a basic compound such as aliphatic or aromatic amines (triethanolamine, guanidine carbonate, dimethylaniline, naphthylamine, etc.) or an alkali-metal or alkaline-earth metal hydroxide or acetate (sodium or potassium acetate, sodium benzoate, etc.). It is generally used in an amount from about 0.001% to 0.05% relative to the weight of reactants present.

The duration of the exchange operation is from 1 to 4 hours; it is generally from about 2 to 3 hours.

When more than 90% of the theoretical amount of methanol has been distilled off, the excess polyol is removed by bringing the temperature of the reaction medium to 230° C.

The polycondensation operation is preferably carried out at a temperature of about 230 to 280° C., preferably of about 240 to 260° C. in another reactor brought beforehand to this temperature and gradually placed under vacuum down to a pressure which may be as low as 10 Pa; a pressure reduction down to about 10 millibar lasts for about 40 minutes.

The polycondensation operation takes place with removal of polyol molecules, this operation being stopped when the motor torque of the stirrer shaft indicates a value equivalent to about 0.5 to 5 newton.metres for a temperature of 250° C. of the reaction mass and a stirring speed of 80 revolutions/minute of an anchor-shaped spindle in a 7.5 litre reactor. The vacuum is then broken with nitrogen and the polymer is poured into a mould; after cooling, the polymer is ground.

When one of the "diacid" monomers is present in the form of diacid or anhydride and the other(s) is(are) in the form of diester(s), the said copolyester oligomers are obtained by first carrying out a transesterification operation of the diester monomers with ethylene glycol under the conditions described above, followed by an esterification operation in the medium of the diacid or anhydride monomer with ethylene glycol, and then polycondensation under the conditions described above, the total amount of ethylene glycol being divided between the two operations (transesterification and esterification).

If necessary, the esterification operation is carried out by adding, to the reaction medium resulting from the transesterification operation, monomer in diacid or anhydride form and ethylene glycol placed in suspension beforehand, at a temperature corresponding to that at the end of the exchange; the introduction period is about 1 hour.

This esterification operation is carried out at a temperature of about 230 to 280° C. preferably of about 250 to 260° C. in the presence of a catalyst of the same type as the transesterification catalyst, and an etherification-limiting agent.

The operation is carried out in the presence of the same types of catalyst and of etherification-limiting agent as those used in the transesterification operation, and in the same proportions.

The reaction is carried out with removal of water, which is removed from the reactor at the same time as the excess polyol.

This type of preparation process is described in particular in patent application WO 95/32997 (Rhône-Poulenc Chimie).

Preferably, the composition according to the invention comprises between 0.5 and 15% by weight, relative to the total weight of the composition, of hydrophilic gelling material, more preferably between 2 and 10% by weight.

The composition according to the invention is a cosmetic composition which can be applied to the skin, mucous membranes, the hair or superficial body growths.

The composition according to the invention consists of an aqueous gel which can also comprise a fatty phase. The fatty phase can comprise volatile or non-volatile oils, or waxes which are common in cosmetics, of animal, plant, mineral or synthetic origin, alone or as mixtures, in particular volatile or non-volatile silicone oils, in particular polysiloxanes. In this case, the fatty phase can be dispersed in the gel, in particular in the form of an emulsion of oil-in-water type. The amount of fatty phase in the compositions according to the invention is preferably less than or equal to 10% by weight relative to the total weight of the composition, more preferably less than or equal to 5% by weight.

The composition according to the invention can comprise additives and/or active agents that are common in cosmetics, it being understood that a person skilled in the art will know how to determine the amounts of these additives and active agents which may be added to the composition according to the invention so as not to adversely affect the rheological profile of the gel constituting it.

The common cosmetic additives are, in particular, fragrances, dyes, odour absorbers, additives for stabilizing the composition, such as preserving agents, UVA and/or UVB screening agents, hydrophilic and/or lipophilic antioxidants, chelating agents, etc. The amounts of these various adjuvants are those used conventionally in the field considered, and, for example, from 0.01 to 5% by weight relative to the total weight of the composition. Depending on their nature, these adjuvants can be introduced into the aqueous phase or into the fatty phase when the composition also comprises a fatty phase.

The composition according to the invention can also comprise hydrophilic and/or lipophilic active agents that are common in cosmetics, in particular anti-free-radical agents, alpha- or beta-hydroxy acids, UVA and/or UVB screening agents, ceramides, antidandruff agents such as octopirox or zinc pyrithione, antiacne agents such as retinoic acid or benzoyl peroxide, agents for combating hair loss such as minoxidil, antifungal or antiseptic agents, etc. It can also comprise electrolytes, more particularly strontium, magnesium or manganese salts, such as, for example, strontium chloride.

Needless to say, the composition according to the invention will not comprise any constituents liable to impair the specific rheological properties of the aqueous gel constituting it.

The composition according to the invention is preferably a topical, cosmetic or pharmaceutical composition, intended to be applied to the skin, mucous membranes, the hair or superficial body growths.

It can be used for all the usual dermocosmetic uses, and in particular as a body hygiene composition, as a hair composition, as a make-up composition or as a care composition. This composition is preferably intended to be applied to the hair.

For use as a hair composition, owing to the specific rheological properties of the gel constituting it, the composition according to the invention affords a good styling effect and discipline to the hairstyle.

In order to obtain a fixing effect or to improve the styling and disentangling effect, a fixing material or a conditioning material can be added to the composition according to the invention. These fixing or conditioning materials can be used in amounts of between 0.01 and 15% by weight relative to the total weight of the composition, preferably between 0.1 and 8% by weight.

The composition according to the invention can also comprise haircare active agents and/or sheen-enhancing agents and/or hair dyes. These active agents and/or hair agents can be used in amounts of between 0.01 and 20% by weight relative to the total weight of the composition according to the invention.

The fixing materials which are useful according to the invention consist essentially of at least one fixing polymer, alone or in combination with common cosmetic additives, for example plasticizers, or neutralizing agents. According to the invention, any known fixing polymer per se can be used. It is possible in particular to use a fixing polymer chosen from anionic, cationic, amphoteric and nonionic polymers and mixtures thereof. If necessary, the anionic or amphoteric fixing polymers can be partially or totally neutralized. The neutralizing agents are, for example, sodium hydroxide, potassium hydroxide, 2-amino-2-methyl-1-proparol, monoethanolamine, triethanolamine or triisopropanolamine, and inorganic or organic acids such as hydrochloric acid or citric acid. The fixing polymers can be used in solubilized form or in the form of dispersions of solid polymer particles.

The cationic fixing polymers which can be used according to the present invention are preferably chosen from polymers comprising primary, secondary, tertiary and/or quaternary amine groups forming part of the polymer chain or directly connected thereto, and having a molecular weight of between 500 and about 5,000,000 and preferably between 1000 and 3,000,000.

The anionic fixing polymers generally used are polymers comprising groups derived from carboxylic, sulphonic or phosphoric acid and have a weight-average molecular weight of between about 500 and 5,000,000. Such polymers are described in particular in the patents and patent applications DE 2,330,956, FR 1,222,944, FR 1,564,110, FR 1,580,545, FR 2,198,719, FR 2,265,782, FR 2,265,781, FR 2,350,384, FR 2,357,241, FR 2,439,798, GB 839,805, LU 75370, LU 75371, U.S. Pat. Nos. 2,047,398, 2,723,248, 2,102,113 and 4,128,631. They are chosen in particular from the products sold under the names Versicol® E or K by the company Allied Colloid, Amerhold® DR 25 by the company Amerchol, Quadramer® by the company American Cyanamid, Aristoflex® A, Luviflex® VBM 70, Luvimer® 100 P or MAEX or MAE, Ultrahold® and Ultrahold® Strong by the company BASF, Cosmedia® Polymer HSP-1180 by the company Henkel, Reten® 421, 423 or 425 by the company Hercules; Acrylidone® LM, Gantrez® AN or ES and Advantage® CP by the company ISP, Flexan® 500, Flexan® 130 and Resins 28-29-30, 26-13-14 or 28-13-10 by the company National Starch, Acudyne® 255 by the company Rohm & Haas, Eudragit® L by the company Rohm Pharma and Stepanhold® Extra by the company Stepan, or the crotonic acid/vinyl acetate/vinyl t-butylbenzoate copolymer from the company Chimex.

The amphoteric fixing polymers which can be used in accordance with the invention are described in particular in the patents FR 1,400,366 and U.S. Pat. No. 3,836,537. They are chosen in particular from the products referred to by the CTFA (4th edition, 1991) name of octylacrylamide/acrylates/butylaminoethyl methacrylate copolymer and those sold under the names Amphomer®, Amphomer® LV 71 or Lovocryl® 47 by the company National Starch, Diaformer® Z301 by the company Sandoz and Evalsan® by the company Jan Dekker.

The conditioning materials which are useful according to the invention consist essentially of the conditioning materials which are common in cosmetics. They are chosen in particular from cationic surfactants, anionic or nonionic or cationic or amphoteric polymers, proteins, protein hydrolysates, ceramides, pseudoceramides, fatty acids containing linear or branched $C_{16}$–$C_{40}$ chains such as 18-methyleicosanoic acid, and silicones which may be linear or branched, organomodified or otherwise, volatile or non-volatile and soluble or insoluble in the medium, and mixtures thereof.

The conditioners of cationic polymer type which are useful according to the invention can be chosen from all those already known per se as improving the cosmetic properties of the hair, i.e., in particular, those described in patent applications EP 0,337,354, FR 2,270,846, FR 2,383, 660, FR 2,598,611, FR 2,470,596 and FR 2,519,863. Among all the cationic polymers which can be used in the context of the present invention, it is preferred to use quaternary cellulose ether derivatives such as the products sold under the name JR 4000® by the company Union Carbide Corporation, or under the name Celquat® L 200 by the company National Starch, cyclopolymers, in particular diallyldimethylammonium salt homopolymers and copolymers of diallyldimethylammonium salt and of acrylamide, in particular the chlorides, sold under the names Merquat® 100, Merquat® 550 and Merquat® S by the company Merck, cationic polysaccharides and more particularly the guar gums modified with 2,3-epoxypropyltrimethylammonium chloride which are sold, for example, under the name Jaguar C13S® by the company Meyhall.

Among the sheen-enhancing agents, mention may be made of non-volatile arylsilicones, in particular polyalkylarylsiloxanes such as the phenylsilicone sold under the name DC 556 by the company Dow Corning, or diphenyldimethicone sold under the name Mirasil® DPDM by the company Rhône-Poulenc.

Among the hair dyes which may be mentioned in particular are direct dyes. Among those conventionally used, mention may be made of nitrobenzene dyes, such as nitrophenylenediamines, nitrodiphenylamines, nitroanilines, nitrophenol ethers, nitrophenols or nitropyridines, anthraquinone dyes, monoazo or diazo dyes, triarylmethane dyes, azine dyes, acridine dyes and xanthene dyes or alternatively metalliferous dyes. These direct dyes, in salified or base form, are generally present in the composition according to the invention in proportions which can range from about 0.001 to about 10%, and preferably from about 0.05 to about 5%, by weight relative to the total weight of the composition.

The composition according to the invention is preferably intended to be vaporized.

The present invention thus also relates to a device consisting of a container containing a composition as defined above and a means for distributing the said composition.

According to the invention, a distinction may be made between devices of the pump-dispenser bottle type, for which the means for distributing the cosmetic composition is a pump, and aerosol devices, for which the cosmetic composition also comprises a suitable amount of propellant, the product being distributed by means of an appropriate distribution valve system controlled by a distribution head, itself comprising a nozzle via which the aerosol composition is vaporized.

The propellant consists of the compressed or liquefied gases usually used for the preparation of aerosol compositions. Compressed air, carbon dioxide or nitrogen, or alternatively a gas which is soluble or insoluble in the composition, such as dimethyl ether, halogenated or non-halogenated hydrocarbons and mixtures thereof, will preferably be used.

The amount of propellant in the cosmetic composition will be sufficient to allow distribution of the composition. It will advantageously be between 20 and 50% by weight relative to the total weight of the composition.

The present invention also relates to the cosmetic use of a composition as defined above.

Lastly, the invention relates to a cosmetic treatment process for the skin, mucous membranes or superficial body growths, in which the composition as defined above is applied to the skin, mucous membranes or superficial body growths. The composition is preferably applied by means of the device according to the invention.

The examples below illustrate the invention without, however, limiting its scope. The percentages of the constituents in the various compositions in the examples are expressed on a weight basis relative to the total weight of the composition. The expression "am" means active material.

EXAMPLE 1

Preparation of a Terephthalic Copolyester Oligomer

The following reactants are introduced into a 7.5 litre stainless-steel reactor fitted with an anchor-shaped stirrer rotating at 80 rev/min, connected to a Kyowa torsion meter, a jacket for circulating a heat-exchange liquid, and a distillation column controlled by an electrovalve:

11.47 mol of dimethyl terephthalate 2.53 mol of sodium dimethyl isophthalic-5-sulphonate 39.16 mol of ethylene glycol 54 ppm by weight of titanium, in the form of titanium aminotriethanolate as catalyst and etherification-limiting agent.

The mixture is preheated to 180° C. It is then brought to a temperature of 220° C. over about 130 minutes, in order to distill off more than 90% of the theoretical amount of methanol.

The reaction mixture is then brought to 230° C. over 30 minutes. When the reaction mass has reached this temperature, a suspension having the composition below is introduced over 60 minutes, still at 230° C.:

0.5 mol of isophthalic acid 2.36 mol of terephthalic acid 8 mol of ethylene glycol.

The reaction mass is then brought to a temperature of 250° C. over 60 minutes.

During the period of introduction of the mixture and during the period of heating up to 250° C., a mixture of water and ethylene glycol are distilled off without retrogradation.

The reaction mixture is then transferred into an autoclave preheated to 250° C. and is then placed under a reduced pressure of 100 millibar over 22 minutes. After 2 minutes under these temperature and pressure conditions, the reaction mass is cast and cooled.

The copolyester obtained has the structural characteristics described in Table 1 in which:

"mol % of diacid units" corresponds to the content, in %, of each diacid or diester used relative to the sum total of diacids or diesters used.

"Tp" means: terephthalic unit

"Ip" means: isophthalic unit

"SIp" means: sulphoisophthalic unit

The characteristics of the "glycol" part of the copolyesters are obtained by methanolysis of the products at 190° C. for 16 hours, followed by analysis by the gas chromatography technique and assaying by internal calibration.

"mol % of diol units" corresponds to the content, in %, of oxyethylene units "G", di(oxyethylene) units "2G", tri(oxyethylene) units "3G" and tetra(oxyethylene) units "4G", relative to the sum total of diol units.

"%GT/Σ units" corresponds to the mol % of units of formula (I)

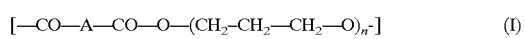

$$[—CO—A—CO—O—(CH_2—CH_2—CH_2—O)_n-] \quad (I)$$

where A is 1,4-phenylene and n=1 relative to the sum total of units of formula (I) where A is 1,4-phenylene, sulpho-1,3-phenylene and optionally 1,3-phenylene and n ranges from 1 to 4 "%GT/Σ units" is calculated by the following formula:

%GT/Σ units=(mol % of Tp units)×(mol % of G units)/100

The molar mass of the polyesters (Mw) is determined by gel permeation chromatography (GPC) in 100% DMAc/LiBr, the results being given in polystyrene equivalents.

| mol % of the diacid units | |
|---|---|
| Tp | 82 |
| Ip | 3 |
| SIp | 15 |
| % GT/Σ units | 46.5 |

| -continued | |
|---|---|
| mol % of the diol units | |
| G | 56.8 |
| 2G | 30.7 |
| 3G | 10 |
| 4G | 2.5 |
| Mw | 8000 |

EXAMPLE 2

Rheological Profile of a Gel Containing 8% of the Oligomer of Example 1

An aqueous gel is prepared by mixing together, without heating, 8% of the oligomer of Example 1 and the remainder to 100% of demineralized water. The fluid gel obtained is poured into a mould and left to stand for 24 hours. After setting to a solid, the rheological profile of the gel obtained is measured:

| | |
|---|---|
| Initial viscosity $V_0$: | 30,000 Pa · s |
| Shear strain $C_1$: | 80 Pa |
| Viscosity $V_2$ at a strain $C_2$ of 105 Pa: | 30 Pa · s |

EXAMPLE 3

Styling Spray in a Pump-dispenser Bottle

The procedure of Example 2 is repeated with the following constituents:

| | |
|---|---|
| Oligomer of Example 1 | 5% am |
| PVP/PA (65/35) copolymer | 2% am |
| Water | qs 100% |

The gel obtained is then packaged in a device consisting of a container and a means of diffusion of pump-dispenser type, sold by the company Coster under the reference MS P 200 Nozzle V06203.

The composition is diffused without difficulty by vaporization, to be applied onto the hair.

EXAMPLE 4

Conditioning Spray in a Pump-dispenser Bottle

The procedure of Example 2 is repeated with the following constituents:

| | |
|---|---|
| Oligomer of Example 1 | 5% am |
| Polyquaternium 4 (sold under the name Celquat ® L200 by the company National Starch) | 2% am |
| Water | qs 100% |

The gel obtained is then packaged in a device consisting of a container and a means of diffusion of pump-dispenser type, sold by the company Coster under the reference MS P 200 Nozzle V06203.

The composition is diffused without difficulty by vaporization, to be applied onto the hair.

EXAMPLE 5

Conditioning Spray in a Pump-dispenser Bottle

The procedure of Example 2 is repeated with the following constituents:

| | |
|---|---|
| Oligomer of Example 1 | 5% am |
| Polyaminosiloxane (sold under the name DC 939 by the company Dow Corning | 2% am |
| Water | qs 100% |

The gel obtained is then packaged in a device consisting of a container and a means of diffusion of pump-dispenser type, sold by the company Coster under the reference MS P 200 Nozzle V06203.

The composition is diffused without difficulty by vaporization, to be applied onto the hair.

EXAMPLE 6

Aerosol Spray

The procedure of Example 2 is repeated with the following constituents:

| | |
|---|---|
| Oligomer of Example 1 | 5% am |
| Demineralized water | 67% |
| Dimethyl ether | qs 100% |

The gel obtained is then packaged in a device consisting of a container and a means of diffusion of aerosol type, itself consisting of a valve of reference number C21326002 from the company Precision and a push-button of reference number 31696440AD87 from the company Precision.

The composition is diffused without difficulty by vaporization, to be applied onto the hair.

What is claimed is:

1. A topical composition comprising an aqueous gel which comprises a hydrophilic gelling material, wherein said gel has rheological properties comprising:

an initial viscosity $V_0$ ranging from 3000 to 50,000 Pa.s, wherein said initial viscosity $V_0$ is stable up to a shear strain $C_1$, a viscosity $V_2$ after shear at a strain $C_2$, wherein a ratio of $V_0/V_2$ is greater than or equal to 1000, and a difference of $C_2-C_1$ less than or equal to 100 Pa; wherein said hydrophilic gelling material is a hydrophilic gelling polymer chosen from at least one water-soluble and water-dispersible terephthalic copolyester oligomer comprising dicarboxylate repeating units of formula (I):

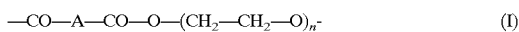

—CO—A—CO—O—(CH$_2$—CH$_2$—O)$_n$-    (I)

wherein

A is chosen from 1,4-phenylene and sulfo-1,3-phenylene groups, and optionally, 1,3-phenylene groups, n ranges from 1 to 4, at least 35 mol % of said units of formula (I) are units of formula (I) wherein A is a 1,4-phenylene group and n is equal to 1, at least 7 mol % of said units of formula (I) are units of formula (I) wherein A is a sulfo-1,3-phenylene group, and the weight-average molecular mass of said at least one copolyester oligomer is less than 20,000 polystyrene equivalents, as measured by gel permeation chromatography in dimethylacetamide containing $10^{-2}$ N of LiBr, at 100° C., and wherein said hydrophilic gelling material comprises from 0.5 to 15% by weight of the composition relative to the total weight of the composition.

2. The composition according to claim 1, wherein the rheological properties of said gel further comprise a viscosity $V_1$ measured at said shear strain $C_1$, wherein a ratio of $V_0/V_1$ is less than or equal to 2.

3. The composition according to claim 1, wherein said shear strain $C_1$ is greater than or equal to 50 Pa.

4. The composition according to claim 1, wherein a fall in viscosity induced by shear on said gel is not immediately reversible.

5. The composition according to claim 1, wherein up to 20% of said units of formula (I) are units of formula (I) wherein A is a 1,3-phenylene group.

6. The composition according to claim 5, wherein up to 5% of said units of formula (I) are units of formula (I) wherein A is a 1,3-phenylene group.

7. The composition according to claim 1, wherein at least 40 mol % of said units of formula (I) are units of formula (I) wherein A is a 1,4-phenylene group and n is equal to 1.

8. The composition according to claim 7, wherein from 40 to 90 mol % of said units of formula (I) are units of formula (I) wherein A is a 1,4-phenylene group and n is equal to 1.

9. The composition according to claim 1, wherein at least 10 mol % of said units of formula (I) are units of formula (I) wherein A is a sulfo-1,3-phenylene group.

10. The composition according to claim 9, wherein from 10 to 25 mol % of said units of formula (I) are units of formula (I) wherein A is a sulfo-1,3-phenylene group.

11. The composition according to claim 1, wherein said at least one copolyester oligomer has end groups independently chosen from groups of formula (I'):

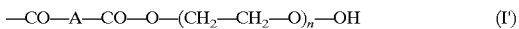

—CO—A—CO—O—(CH$_2$—CH$_2$—O)$_n$—OH    (I')

wherein

A and n are defined as in claim 1.

12. The composition according to claim 1, wherein said at least one copolyester oligomer has end groups indepentently chosen from

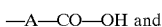

—A—CO—OH and

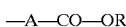

—A—CO—OR wherein A is defined as in claim 1 and R is a $C_1$–$C_4$ alkyl group.

13. The composition according to claim 1, wherein said at least one copolyester oligomer has a weight-average molecular mass of less than 15,000 polystyrene equivalents, as measured by gel permeation chromatography in dimethylacetamide containing $10^{-2}$ N of LiBr, at 100° C.

14. The composition according to claim 1, wherein said at least one copolyester oligomer has a weight-average molecular mass ranging from 5000 and 14,000 polystyrene equivalents, as measured by gel permeation chromatography in dimethylacetamide containing $10^{-2}$ N of LiBr, at 100° C.

15. The composition according to claim 1, wherein said at least one copolyester oligomer has a weight-average molecular mass ranging from 8000 to 10,000 polystyrene equivalents, as measured by gel permeation chromatography in dimethylacetamide containing $10^{-2}$ N of LiBr, at 100° C.

16. The composition according to claim 1, wherein said hydrophilic gelling material comprises from 2 to 10% by weight of the composition relative to the total weight of the composition.

17. The composition according to claim 1, wherein said gel further comprises a fatty phase.

18. The composition according to claim 17, wherein said fatty phase is chosen from volatile oils, non-volatile oils, and waxes of animal, plant, mineral, and synthetic origin.

19. The composition according to claim 1, further comprising at least one hair care or hair styling ingredient chosen from fixing materials, conditioning materials, active agents for haircare, sheen-enhancing agents, and hair dyes.

20. A device comprising:
a container containing a composition comprising an aqueous gel which comprises a hydrophilic gelling material, wherein said gel has rheological properties comprising:
an initial viscosity $V_0$ ranging from 3000 to 50,000 Pa.s, wherein said initial viscosity $V_0$ is stable up to a shear strain $C_1$,
a viscosity $V_2$ after shear at a strain $C_2$, wherein a ratio of $V_0/V_2$ is greater than or equal to 1000, and
a difference of $C_2-C_1$ is less than or equal to 100 Pa, and
a means for distributing said composition; wherein said hydrophilic gelling material is a hydrophilic gelling polymer chosen from at least one water-soluble and water-dispersible terephthalic copolyester oligomer comprising dicarboxylate repeating units of formula (I):

$$-CO-A-CO-O-(CH_2-CH_2-O)_n- \quad (I)$$

wherein
A is chosen from 1,4-phenylene and sulfo-1,3-phenylene groups, and optionally, 1,3-phenylene groups,
n ranges from 1 to 4
at least 35 mol % of said units of formula (I) are units of formula (I) wherein A is a 1,4-phenylene group and n is equal to 1,
at least 7 mol % of said units of formula (I) are units of formula (I) wherein A is a sulfo-1,3-phenylene group, and
the weight average molecular mass of said at least one copolyester oligomer is less than 20,000 polystyrene equivalents, as measured by gel permeation chromatography in dimethylacetamide containing $10^{-2}$ N of LiBr, at 100° C.,
and wherein said hydrophilic gelling material comprising from 0.5 to 15% by weight of the composition relative to the total weight of the composition.

21. The device according to claim 20 wherein said means for distributing said composition is a pump-dispenser.

22. The device according to claim 21, wherein a maximum value of shear strain $C_1$ is less than or equal to 150 Pa.

23. The device according to claim 20, wherein said means for distributing said composition is an aerosol device.

24. The device according to claim 23, wherein a maximum value of shear strain $C_1$ is less than or equal to 200 Pa.

25. The device according to claim 23, wherein said composition further comprises a suitable amount of propellant and wherein said composition is distributed by means of an appropriate distribution valve system controlled by a distribution head, wherein said distribution head comprises a nozzle which vaporizes said composition.

26. The device according to claim 25, wherein said propellant is chosen from compressed gas and liquefied gas.

27. The device according to claim 26, wherein said propellant is chosen from compressed air, carbon dioxide, and nitrogen.

28. The device according to claim 25, wherein said propellant is chosen from gases which are soluble or insoluble in said composition.

29. The device according to claim 28, wherein said gases are chosen from dimethyl ether, halogenated hydrocarbons, and non-halogenated hydrocarbons.

30. The device according to claim 25, wherein said amount of propellant ranges from 20 to 50% by weight relative to the total weight of the composition.

31. A process for cosmetically treating at least one of skin, mucous membranes, hair and superficial body growths, said process comprising applying to said skin, mucous membranes, hair or superficial body growths a composition comprising an aqueous gel which comprises a hydrophilic gelling material, wherein said gel has rheological properties comprising:
an initial viscosity $V_0$ ranging from 3000 to 50,000 Pa.s, wherein said initial viscosity $V_0$ is stable up to a shear strain $C_1$,
a viscosity $V_2$ after shear at a strain $C_2$, wherein a ratio of $V_0/V_2$ is greater than or equal to 1000, and
a difference of $C_2-C_1$ is less than or equal to 100 Pa; wherein said hydrophilic gelling material is a hydrophilic gelling polymer chosen from at least one water-soluble and water-dispersible terephthalic copolyester oligomer comprising dicarboxylate repeating units of formula (I):

$$-CO-A-CO-O-(CH_2-CH_2-O)_n- \quad (I)$$

wherein
A is chosen from 1,4-phenylene and sulfo-1,3-phenylene groups, and optionally, 1,3-phenylene groups,
n ranges from 1 to 4
at least 35 mol % of said units of formula (I) are units of formula (I) wherein A is a 1,4-phenylene group and n is equal to 1,
at least 7 mol % of said units of formula (I) are units of formula (I) wherein A is a sulfo-1,3-phenylene group, and
the weight average molecular mass of said at least one copolyester oligomer is less than 20,000 polystyrene equivalents, as measured by gel permeation chromatography in dimethylacetamide containing $10^{-2}$ N of LiBr, at 100° C.,
and wherein said hydrophilic gelling material comprising from 0.5 to 15% by weight of the composition relative to the total weight of the composition.

32. A process for cosmetically treating at least one of skin, mucous membranes, hair and superficial body growths, said process comprising:
applying to said skin, mucous membranes, hair or superficial body growths a composition comprising an aqueous gel which comprises a hydrophilic gelling material, wherein said gel has rheological properties comprising:
an initial viscosity $V_0$ ranging from 3000 to 50,000 Pa.s, wherein said initial viscosity $V_0$ is stable up to a shear strain $C_1$,
a viscosity $V_2$ after shear at a strain $C_2$, wherein a ratio of $V_0/V_2$ is greater than or equal to 1000, and
a difference of $C_2-C_1$ is less than or equal to 100 Pa,
wherein said composition is applied by means of a device comprising a container containing said composition and a means for distributing said composition; wherein said hydrophilic gelling material is a hydrophilic gelling polymer chosen from at least one water-soluble and water-dispersible terephthalic copolyester oligomer comprising dicarboxylate repeating units of formula (I):

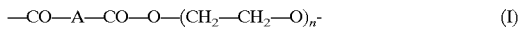
—CO—A—CO—O—(CH$_2$—CH$_2$—O)$_n$-      (I)

wherein

A is chosen from 1,4-phenylene and sulfo-1,3-phenylene groups, and optionally, 1,3-phenylene groups, n ranges from 1 to 4 at least 35 mol % of said units of formula (I) are units of formula (I) wherein A is a 1,4-phenylene group and n is equal to 1, at least 7 mol % of said units of formula (I) are units of formula (I) wherein A is a sulfo-1,3-phenylene group, and the weight average molecular mass of said at least one copolyester oligomer is less than 20,000 polystyrene equivalents, as measured by gel permeation chromatography in dimethylacetamide containing $10^{-2}$ N of LiBr, at 100° C., and wherein said hydrophilic gelling material comprising from 0.5 to 15% by weight of the composition relative to the total weight of the composition.

33. The process according to claim 32, wherein said composition is vaporizable.

* * * * *

UNITED STATES PATENT AND TRADEMARK OFFICE
CERTIFICATE OF CORRECTION

PATENT NO. : 6,803,047 B1 Page 1 of 1
DATED : October 12, 2004
INVENTOR(S) : Christine Dupuis It is certified that error appears in the above-identified patent and that said Letters Patent is hereby corrected as shown below:

Column 14,
Line 48, "10-2" should read -- $10^2$ --.

Signed and Sealed this

Twenty-fifth Day of January, 2005

JON W. DUDAS
*Director of the United States Patent and Trademark Office*